(12) United States Patent
Gottlieb et al.

(10) Patent No.: US 6,991,096 B2
(45) Date of Patent: Jan. 31, 2006

(54) PACKAGING SYSTEM

(75) Inventors: Rebecca Gottlieb, Culver City, CA (US); Aaron Swanson, Los Angeles, CA (US); Bahar Reghabi, Marina del Rey, CA (US); Kevin Branch, Northridge, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 10/331,136

(22) Filed: Dec. 27, 2002

(65) Prior Publication Data

US 2004/0060260 A1 Apr. 1, 2004

Related U.S. Application Data

(60) Provisional application No. 60/414,288, filed on Sep. 27, 2002.

(51) Int. Cl.
*A61M 25/00* (2006.01)
*B65D 81/32* (2006.01)

(52) U.S. Cl. .................. 206/210; 206/364; 206/438
(58) Field of Classification Search ................ 206/210, 206/363, 364, 365, 366, 438, 570, 571
See application file for complete search history.

(56) References Cited

U.S. PATENT DOCUMENTS

| 3,967,728 A | 7/1976 | Gordon et al. |
| 4,863,016 A | 9/1989 | Fong et al. |

OTHER PUBLICATIONS

PCT International Search Report as issued in International Application No. PCT/US03/29014, Mailing date Mar. 29, 2004.

*Primary Examiner*—David T. Fidei
(74) *Attorney, Agent, or Firm*—Foley & Lardner LLP (57) ABSTRACT

A packaging system for hydrating sterile devices without comprising the integrity of the sterilization. The packaging system may include an enclosure for enclosing a device requiring hydration, a container containing a hydrate, a base located within the interior of the enclosure and an activating member located within the interior of the enclosure. The container and the device may be located within a receptacle. The receptacle may rest on the base and the activating member may be affixed on top of the receptacle. A force may be exerted on an exterior portion of the enclosure such that the activating member pushes on the receptacle and crushes or ruptures the container. The hydrate located within the container is then released to the device, thereby hydrating the device without breaking the seal of the enclosure. The sterilized environment is therefore maintained and the device is hydrated.

25 Claims, 12 Drawing Sheets

PACKAGING SYSTEM

CROSS-REFERENCE TO RELATED APPLICATIONS

Embodiments of the present invention relate to U.S. Provisional Application Ser. No. 60/414,288, filed Sep. 27, 2002, entitled "Packaging System," which is incorporated by reference herein and is a basis for a claim of priority.

BACKGROUND

1. Field of the Invention

This invention relates to the field of packaging and, in particular, to packaging, systems and processes capable of hydrating contents of a package or exchanging fluids within the package while, in some embodiments, maintaining a sterile environment within the package.

2. Description of Related Art

Many devices in the sensing arts and other areas of technology require hydration for proper operation. Although such devices may be stored in a dehydrated state for a variety of reasons, hydration is required to effectively utilize the devices.

Some applications also require that sensors be sterilized, such as, for example, an in vivo biological parameter sensor. Traditionally, the combination of hydrating and sterilizing an in vivo biological parameter sensor has been troublesome. Sterilization of in vivo biological parameter sensors is frequently accomplished by exposure of the sensor to ethylene oxide (EtO) gas. However, if a sensor has been hydrated and is then sterilized using EtO, exposure of the hydrate to EtO could cause the hydrate to become toxic, which, in turn, would cause the sensor to become toxic and would render it unsuitable for in vivo implantation. Thus, hydration and sterilization have traditionally been at odds with each other.

Other applications require that a sensor or other device requiring hydration for activation be hydrated by the sensor manufacturer. Because state of the art sensor technology may place too great a demand on the capabilities of an end user to effectively hydrate a sensor, sensor hydration is best accomplished by the manufacturer having sophisticated capabilities. However, many devices tend to lose shelf life once hydration has been effected. For those devices that have been hydrated and then sit on the shelf of the end user for an extended period of time before use, the effective life of the device may be limited or even over by the time the device is utilized.

Accordingly, there is a need in industry to provide a system for hydrating sterilized devices without compromising the integrity of the sterilization. There is also a need in industry to provide a system for hydrating devices that allows for maximum shelf life of the device. The present invention satisfies these needs.

SUMMARY

Embodiments of the present invention relate to systems and processes for hydrating sterilized devices without compromising the integrity of the sterilization. Further embodiments of the present invention relate to systems and processes for hydrating devices that allow for maximum shelf life of the device.

A packaging system and system according to an embodiment of the present invention may include an enclosure for enclosing a device requiring hydration and a container containing a hydrate. The container may be located within the packaging system adjacent to the device. The container releases the hydrate to the device. The packaging system may also include a receptacle located within an interior of the enclosure, a base located within the interior of the enclosure and underneath the receptacle and an activating member located within the interior of the enclosure and on top of the receptacle.

According to an embodiment of the present invention, the container and the device requiring hydration may be located within the interior of the receptacle. Also, the activating member may exert a force on the container to release the hydrate to the device. The force may be applied to an external portion of the enclosure and may be transferred to the container via the activating member.

According to an embodiment of the present invention, a covering may surround the container. The covering may be a mesh made from any one of a variety of materials, including, but not limited to, nylon, paper, DACRON, cotton, polyester, any natural or manmade fiber, other filtering-type material, foil or other protective material and the like. The container may be an ampule, a bladder, a sponge, or the like.

The device requiring hydration may reside in a first interior portion of the receptacle while the container may reside in a second interior portion of the receptacle. The hydrate may then flow from the second interior portion of the receptacle to the first interior portion of the receptacle. The hydrate may flow through a channel, tube, valve or other mechanism. The hydrate may be a fluid, liquid, gel, gas, sterilant or the like, or a combination of hydrates, and may include, without limitation, drugs, activators, solvents or the like.

According to an embodiment of the present invention, a method for hydrating a device may include enclosing the device within a package, providing a container containing a hydrate inside the package and causing the container to release the hydrate to the device. Causing the container to release the hydrate may include exerting a force on an activating member, whereby exerting the force on the activating member causes the container to break or to rupture depending on the nature of the container. Before causing the container to release the hydrate to the device, the device and the package may be sterilized with a sterilizing agent, including, but not limited to, a gas, a liquid, radiation or the like. For example, the device and the package may be sterilized with a sterilizing process including, but not limited to, ethylene oxide.

The method for hydrating a device may also include placing the container in a first cavity of a receptacle and placing the receptacle inside the package. The device may placed into a second cavity of the receptacle. A base may be placed inside the package such that the receptacle rests on the base. An activating member may be affixed on top of the receptacle such that a force exerted on an exterior portion of the package works through the activating member to cause the container to release the hydrate.

The method may also include sterilizing the package and the device before causing the container to release the hydrate to the device and hermetically sealing the package. The package and the device may be sterilized with ethylene oxide, radiation or other sterilizing agent.

According to an embodiment of the present invention, a packaging system for bringing elements located in a package into contact with each other may include an enclosure for enclosing a first element, a container containing a second element, the container located within the package adjacent to the first element, a base having an inclined surface located within the enclosure, and a receptacle supported on the inclined surface of the base within the enclosure, wherein the container is operable to release the first element to the second element

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
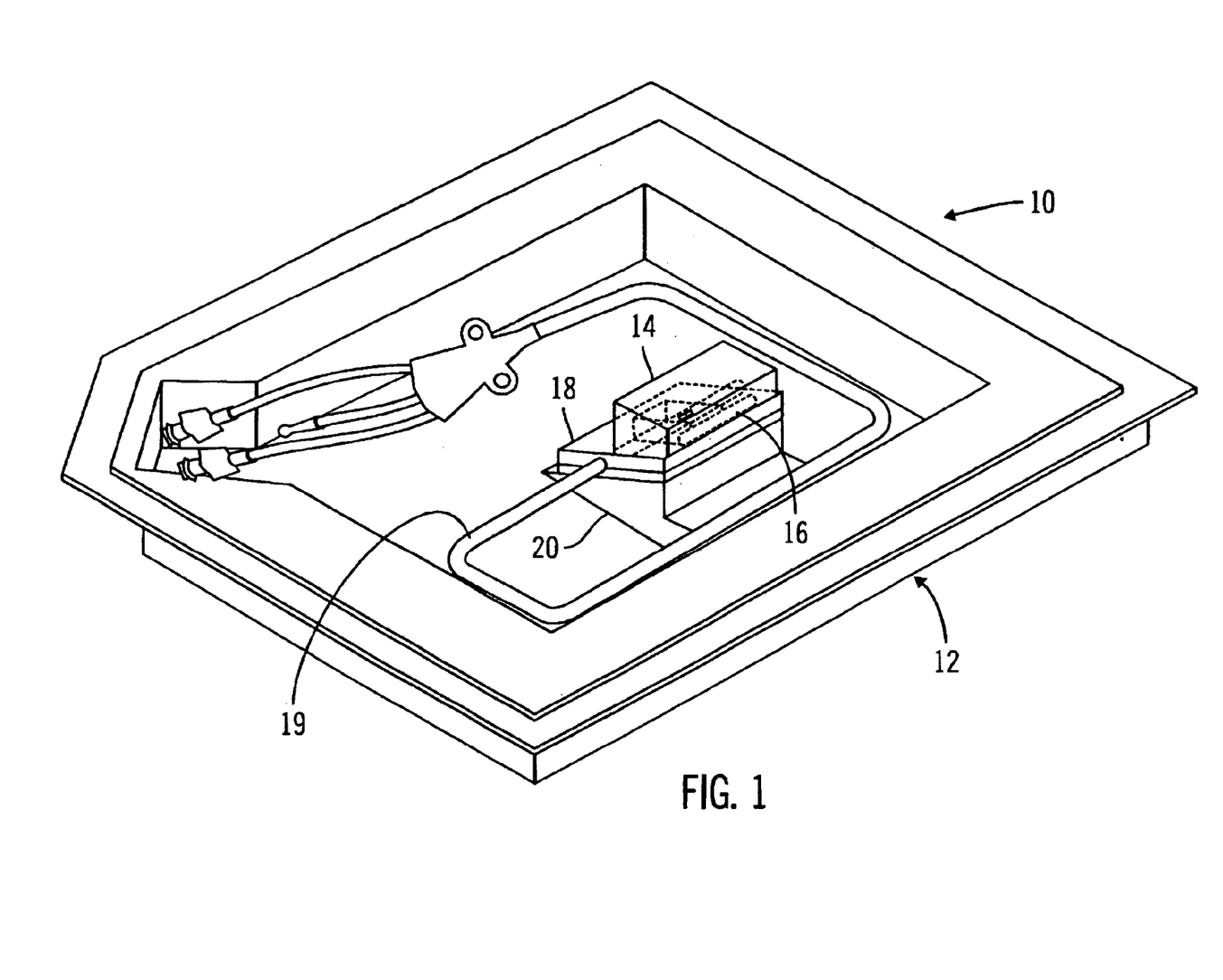
FIG. 1 shows a plan view of a generalized packaging system according to an embodiment of the present invention.

A generalized packaging system 10 according to an embodiment of the present invention is shown in FIG. 1. The packaging system 10 includes, without limitation, an enclosure 12, an activating member 14, a substance container 16 and a receptacle 18. The enclosure 12 may allow sterilant penetration, but not microbe penetration, and generally includes enough space within its interior to house a device requiring hydration in addition to the other elements of the packaging system 10. For example, in the embodiment shown in FIG. 1, the enclosure 12 houses a catheter 19 having a sensing element which must be hydrated. A sensing element suitable for this type of embodiment is disclosed in a patent application entitled "Sensing Apparatus and Process," Ser. No. 10/036,093, filed Dec. 28, 2001, which is hereby incorporated by reference, and in a patent application entitled "Sensor Substrate and Method of Fabricating Same," Ser. No. 10/038,276, filed Dec. 31, 2001, which is also hereby incorporated by reference.

The packaging system 10, however, is not limited to housing catheters or medical devices. The packaging system 10 may house any suitable structure, component or device requiring hydration or activation through exposure to a fluid or other hydrate. In addition, the packaging system 10 may house any elements that must be mixed together or any element to which a catalyst, solvent or activating agent must be added.

The enclosure 12 may be formed into any suitable shape and size. For example, in the embodiment shown in FIG. 1, the enclosure 12 is generally rectangular in shape and has a generally rectangular shaped interior for housing the other elements of the packaging system 10 as well as the device requiring hydration. However, the enclosure 12 may take on any shape or size sufficient for its intended application. Moreover, the interior portion of the enclosure 12, which houses the other elements of the packaging system 10 and the device requiring hydration, may also take on any suitable shape or size, so long as the hydration requirements for the device requiring hydration are met.

The enclosure 12 may be made from any suitable material, such as, but not limited to, opaque or transparent plastic, TYVEK, medical grade papers or the like. The enclosure 12 also includes a cover 13. Additionally, according to an embodiment of the present invention, the enclosure 12 may be hermetically sealed such that the environment within the interior portion of the enclosure 12 remains relatively constant. Accordingly, for applications requiring that the interior of the enclosure 12 be sterilized, an enclosure 12 that is hermetically sealed ensures that the integrity of the sterile environment within the enclosure 12 is not compromised.

Figure 2A:
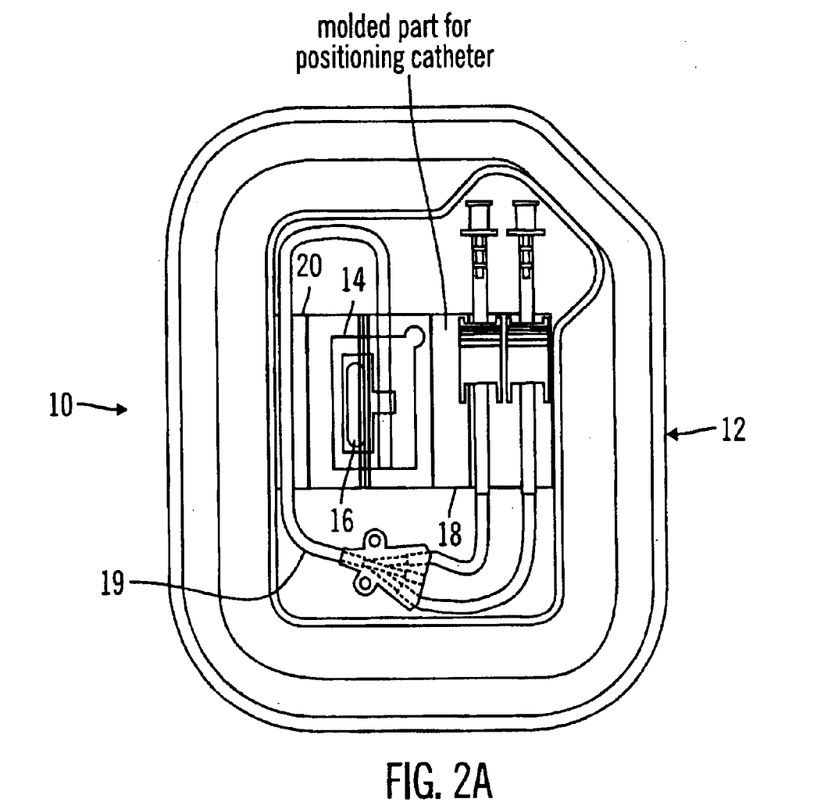
FIG. 2 shows a top view of the packaging system according to an embodiment of the present invention.
Figure 2B:
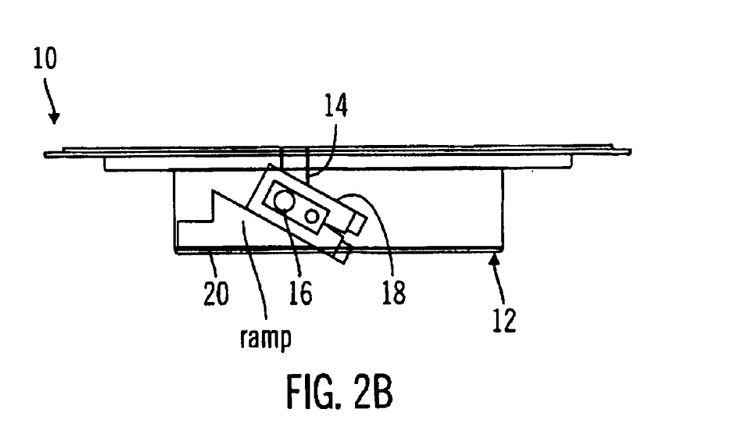

A top view of the packaging system 10 is show in FIG. 2A while a side view of the packaging system 10 is shown in FIG. 2B. FIG. 2A shows how the interior of the enclosure 12 can be a custom geometry to accommodate a particular type of device requiring hydration. Other geometries for accommodating other devices or for accommodating a variety of different devices may be employed in other embodiments of the invention.

Operation of the packaging system 10 can be seen in the view afforded by FIG. 2B. The receptacle 18, which houses the container 16 and the device requiring hydration, such as, for example, an end portion of the catheter 19 shown in FIG. 2A, rests at an angle on the base 20. Affixed on top of the receptacle 18 is the activating member 14. The activating member 14 comprises a generally rigid body that extends from the portion of the receptacle 18 directly above the container 16 to the top cover of the enclosure 12. As will be explained in more detail below, the container 16 may be filled with a sterile buffer or other liquids. An external force, such as that applied by a thumb or finger, for example, may be applied to the activating member 14 by pressing on top of the enclosure 12. Other force applying devices or mechanisms may also be used, such as, for example, a sponge actuator, a pneumatic bulb-type actuator, a sliding member or the like. The force applied will activate the activating member 14 to release liquid from the receptacle 18. In the embodiment shown in FIG. 2B, the force applied will push the activating member 14 to into the receptacle 18, thereby crushing the container 16 and releasing the sterile buffer. Because the receptacle 18 rests on an angle on the base 20, the sterile buffer located within the container 16 will be forced to move by gravity toward the device requiring hydration that has been positioned inside the receptacle 18.

Figure 3:
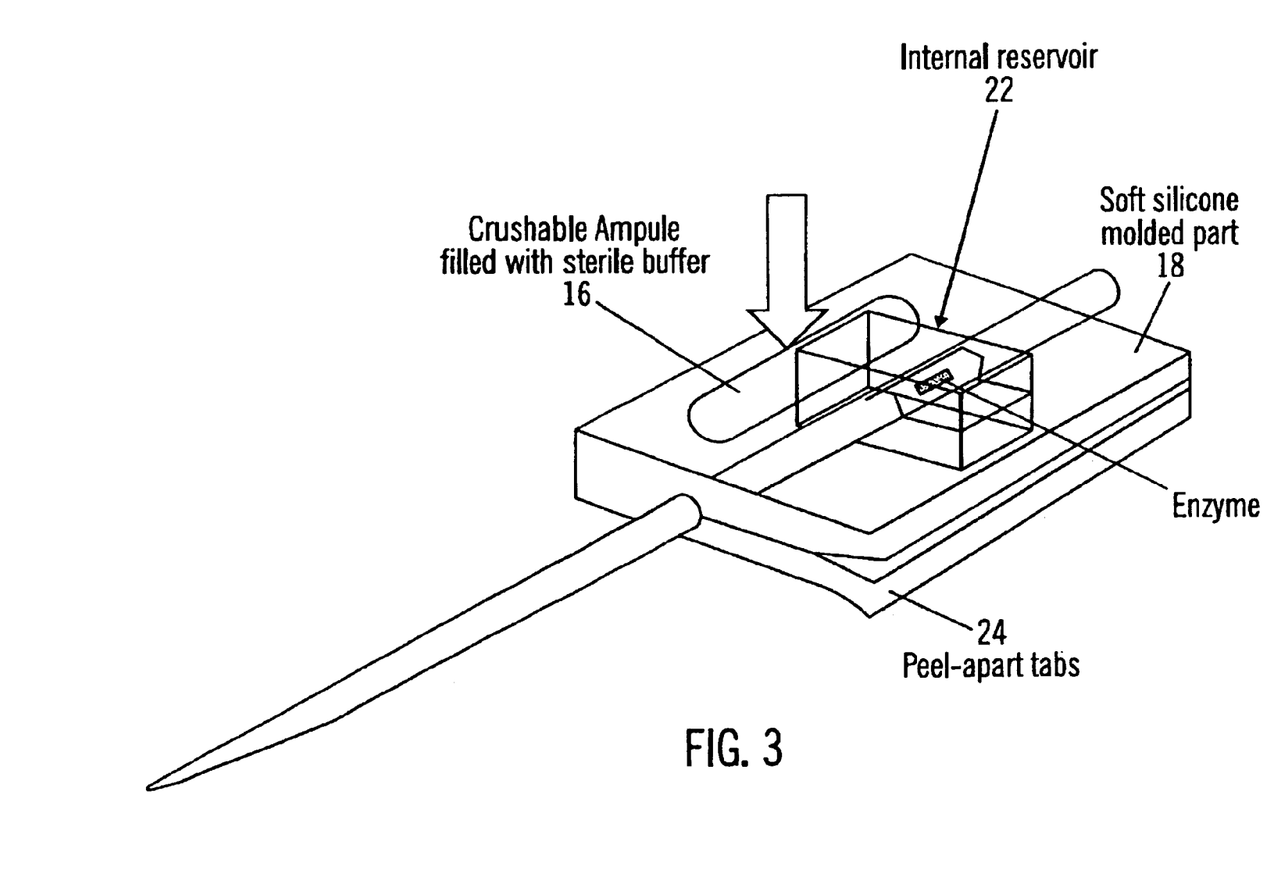
FIG. 3 shows a side view of the packaging system according to an embodiment of the present invention.

Details of the example receptacle 18 may be seen in FIG. 3. The receptacle 18 may be formed from any suitable material that can hold liquid, such as, but not limited to, soft silicone, rubber, plastic and the like. The receptacle 18 may include a top layer 19a of material and a bottom layer 19b of material which define an internal reservoir 22 there between. The internal reservoir 22, which exists within the interior of the receptacle 18, may, for example, comprise a recess or indentation in one or both of the layers 19a and 19b to house a device requiring hydration and provide a place for a hydrating fluid to accumulate. In the embodiment shown in FIG. 3, the receptacle 18 has been fabricated with tabs 24 that allow the receptacle 18 to be pulled apart so that the interior portion of the receptacle 18 may be accessed. The tabs 24 form grip surfaces that allow a user to readily separate the top layer 19a from the bottom layer 19b. The receptacle 18 may also provide an indentation for the container 16, which also exists within the interior of the receptacle 18, to reside.

Figure 4:
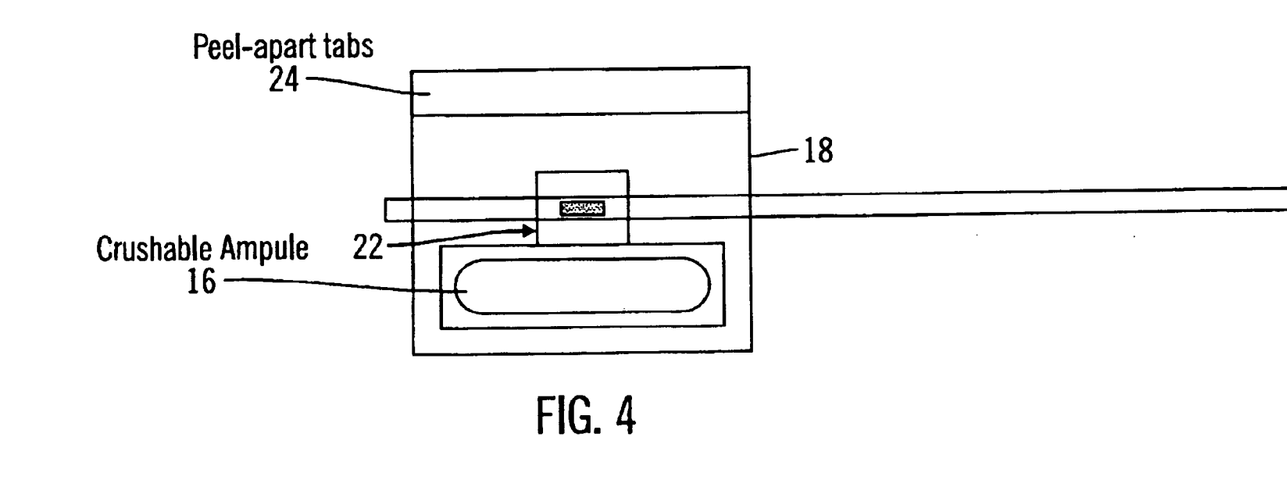
FIG. 4 shows a top view of a receptacle and the relative position of elements within the interior of the receptacle according to an embodiment of the present invention.

FIG. 4 shows a top view of the receptacle 18 and the relative position of elements within its interior. As shown in FIG. 4, the tabs 24 are positioned on one end of the receptacle 18 and are large enough so that a user can pull the tabs apart and reach the internal portion of the receptacle 18. In the embodiment shown in FIG. 4, the reservoir 22 is located generally within the interior of the receptacle 18 at a center portion of the receptacle 18. The container 16 is located within the interior of the receptacle 18 adjacent to the reservoir 22, thereby minimizing the distance that a hydrating fluid located within the container 16 must travel. However, in other embodiments, the position of the elements located within the interior of the receptacle 18 may vary according to the application and the requirements of the device requiring hydration.

Figure 5:
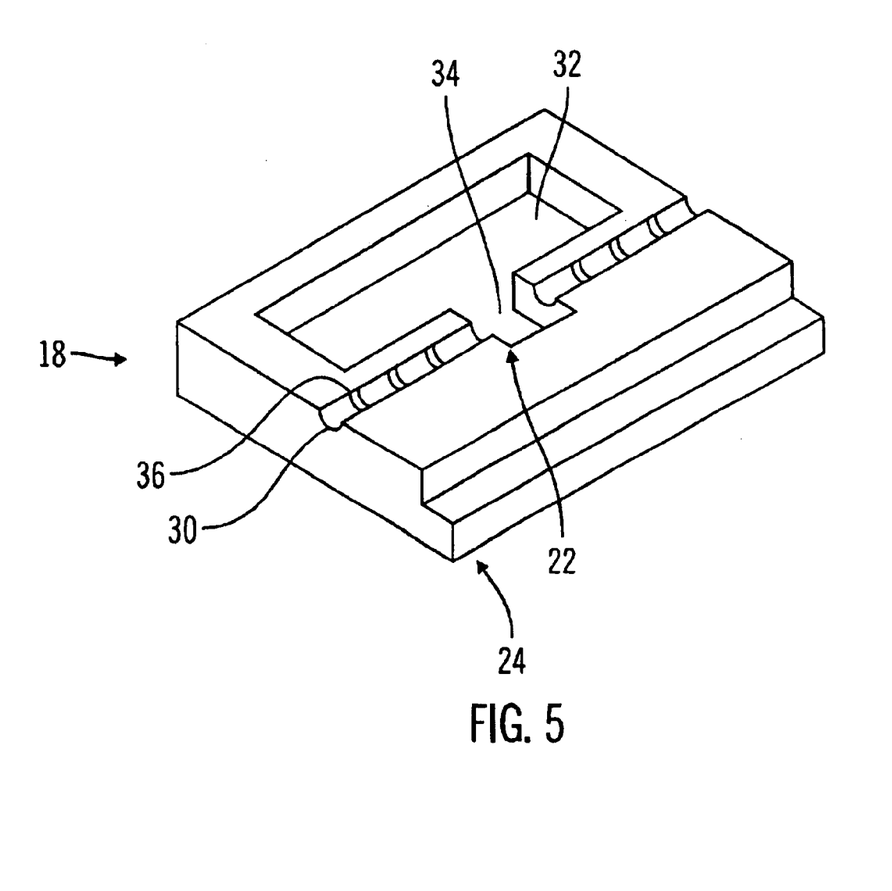
FIG. 5 shows additional details of the receptacle according to an embodiment of the present invention.

Additional details of the example receptacle 18 may be seen in FIG. 5, which shows a bottom one-half portion of the receptacle 18. In the embodiment of the receptacle 18 shown in FIG. 5, the tabs 24 are offset from one another. The offset of the tabs 24 shown in the embodiment of FIG. 5 provides easy separation of the receptacle 18 for a user. Also shown in the embodiment of the receptacle 18 of FIG. 5, a container chamber 32 has been formed to accommodate the container being used for the particular application. The container chamber 32 shown in FIG. 5 is rectangular compression or recess in the bottom layer 19b. In other embodiments, the container chamber 32 may have any shape and size that will accommodate the container being used.

The receptacle 18 shown in FIG. 5 also includes a groove 30 for accommodating a catheter or a catheter-like device. The groove 30 is circular in nature and includes sealing rings, other seals or ribs 36 that provide friction for better gripping of the catheter and that provide seals for better retention of fluids around the catheter. Other means for gripping may be employed in other embodiments, including, but not limited to, treads, protrusion or other discontinuities on the surface of the groove 30 or a groove 30 diameter that is slightly less than the catheter diameter to provide a friction or compression fit. Alternatively, the groove 30 may be replaced by a cutout or cutouts of other shapes and sizes to accommodate the shape and the size of the device requiring hydration.

Figure 6:
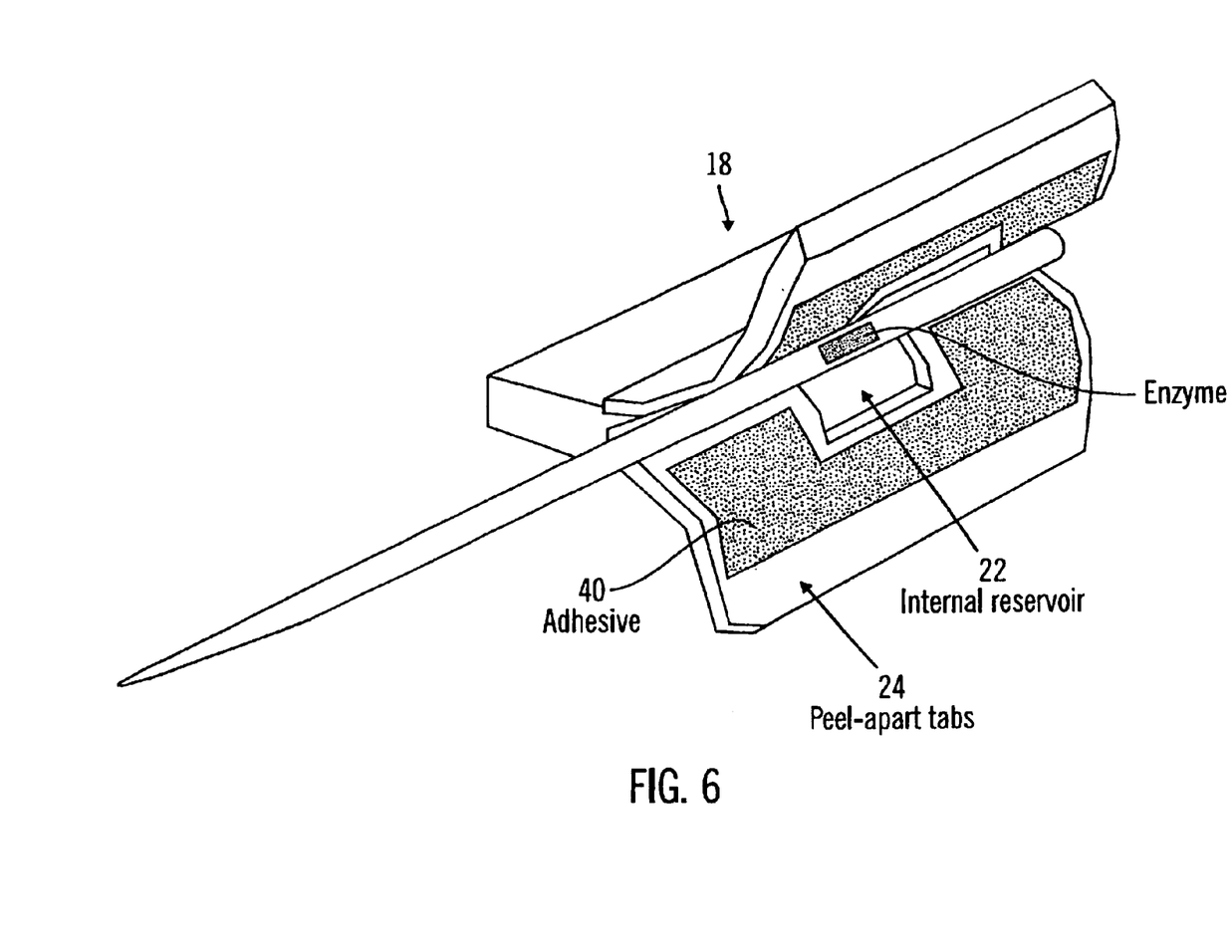
FIG. 6 shows a receptacle with tabs peeled apart according to an embodiment of the present invention.

A receptacle 18 with the tabs 24 peeled apart is shown in FIG. 6. With the tabs 24 peeled apart, the reservoir 22 within the interior of receptacle 18 is exposed. The reservoir 22 is large enough to accommodate the device requiring hydration, in this case, for example, a portion of the catheter. When placed together as shown in FIG. 3, the tabs 24 may be held together in any suitable manner, such as, but not limited to, an adhesive 40 placed upon a portion of the receptacle 18 adjacent to the tabs.

Figure 7A:
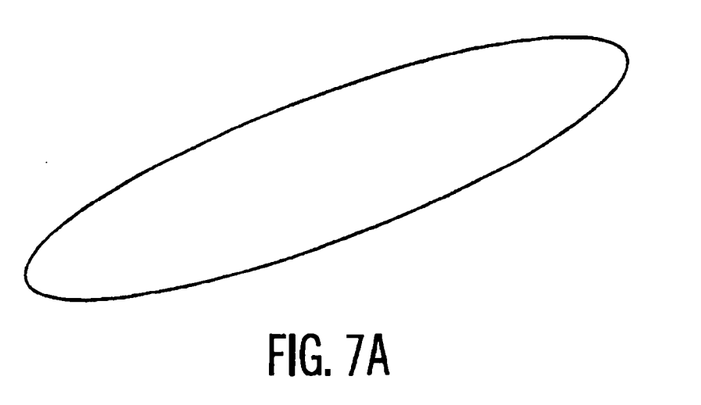
FIG. 7A shows a container according to an embodiment of the present invention.

FIG. 7A shows an embodiment of the container 16. The container 16 may be made from glass, plastic or any material that can be crushed or manipulated with a minimum amount of force. Alternatively, the container 16 need not be sealed container that houses a hydrate. For example, according to other embodiments of the present invention, the container 16 may be a bladder, a sponge, squeeze tube or the like. Moreover, the hydrate need not be highly fluidic. For example, the hydrate may be a gel that exists within a sponge and is squeezed out of the sponge in response to an externally applied force or the hydrate may be a sterilized buffer that has been encapsulated in a glass ampule.

If the container 16 takes the form of a bladder, the bladder may be ruptured or punctured to release the hydrate to the device requiring hydration. For example, the activating member 14 may be fitted with a needle or other piercing element that punctures or ruptures the bladder when a force is applied to the activating member 14.

Figure 7B:
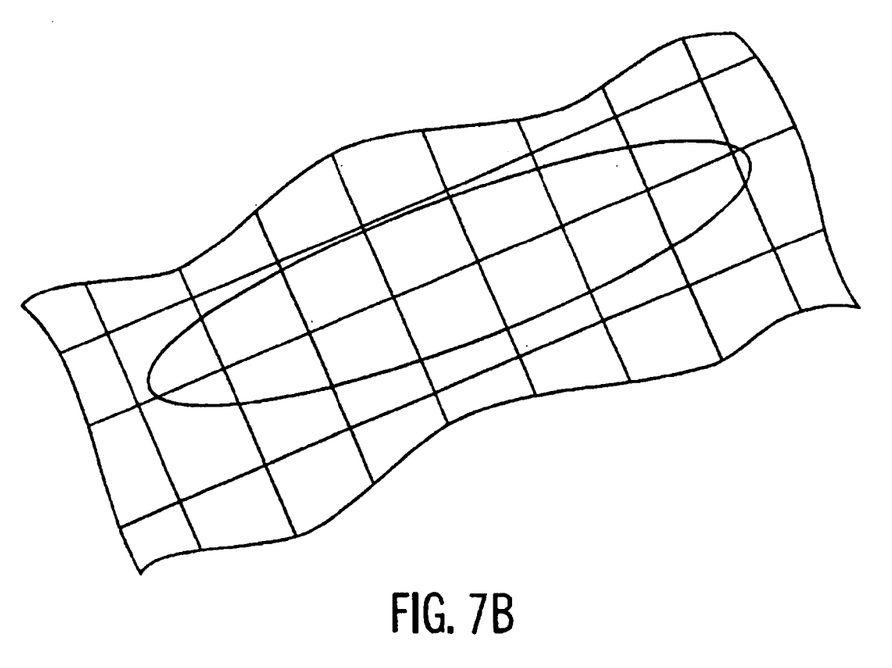
FIG. 7B shows a covering surrounding a container according to an embodiment of the present invention.

In certain example embodiments discussed above, the container 16 comprises a crushable material, such as, but not limited to, a glass or plastic ampule, vial or the like. In such embodiments, a covering 42 may surround the container 16 as shown in FIG. 7B. The covering 42 may be a mesh made from a variety of materials, such as, for example, nylon, fabric, cloth, cotton, paper, plastic or the like. The container 42 is formed such that, if the container 16 is crushed to release the hydrate, the hydrate can flow through the filtering mesh to reach the device requiring hydration, but broken pieces of the container 16 remain within the mesh so as to minimize contamination of the device requiring hydration.

Figure 8:
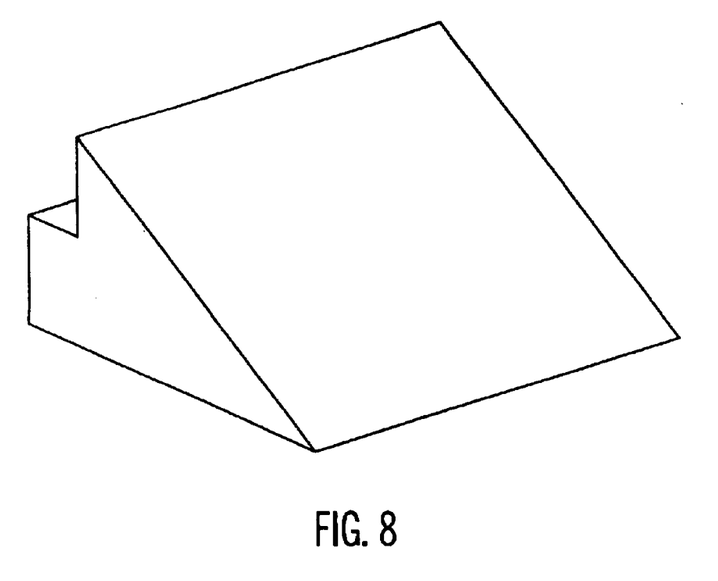
FIG. 8 shows a base according to an embodiment of the present invention.

A base 20 according to an embodiment of the present invention is shown in FIG. 8. The base may include, without limitation, a rigid structure having a flat or an inclined surface 50 and a support surface 52. The inclined surface 50 may elevate at any angle sufficient to direct the hydrate into the device requiring hydration once the container 16 is crushed (or the substance within the container is otherwise released). The support surface 52 is configured to receive accommodate the device requiring hydration. Depending on the requirement of the device, other embodiments need not employ a support surface 52. The actual size and shape of the base 20 may vary according to the size and shape of the device requiring hydration and the size and shape of the enclosure 12. For example, the shape of the base 20 could be circular or "bowl-shaped," with the device requiring hydration residing in the center of the base 20.

Figure 9:
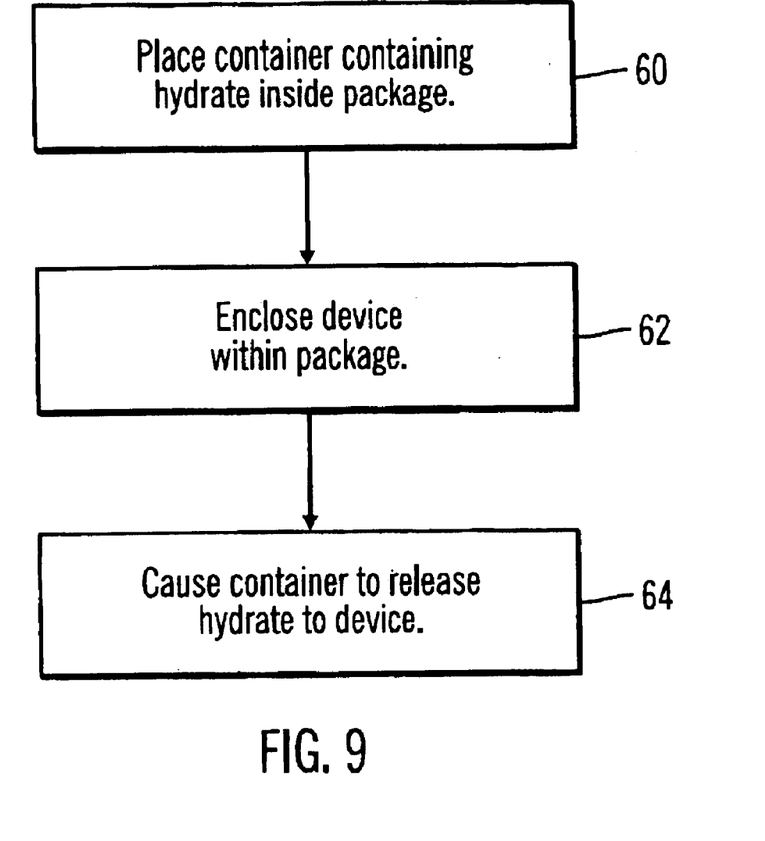
FIG. 9 shows a method for hydrating a device according to an embodiment of the present invention.

A method for hydrating a device according to an embodiment of the present invention is shown in FIG. 9. At step 60, a container 16 containing a hydrate is provided inside a package. At step 62, a device requiring hydration or activation, such as a sensing element, for example, is enclosed within the package. At step 3, and the container 16 releases the hydrate to the device. The container 16 may release the hydrate to the device in response to an external force applied directly or indirectly to the container, for example, through an actuation member 14.

Figure 10:
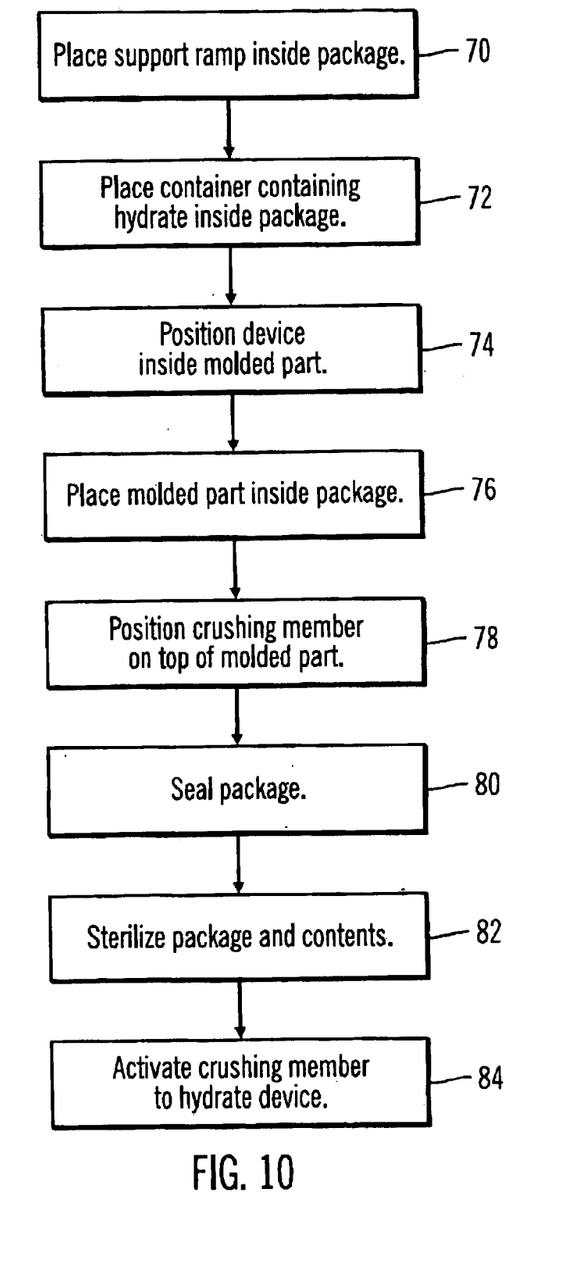
FIG. 10 shows another method for hydrating a device according to an embodiment of the present invention.

A further method for hydrating a device according to an embodiment of the present invention is shown in FIG. 10. At step 70, a support base 20 is placed inside a package. At step 72, a container 16 containing a hydrate is placed inside a receptacle 18 having a cavity for the container. The container 16 is positioned on the support base such that the hydrate inside the container would flow toward the part requiring hydration if the hydrate is released from the container 16.

At step 74, a device requiring hydration is also positioned within the receptacle 18, the device being position adjacent to the container 16. The receptacle 18 may also include a cavity for receiving the device requiring hydration.

At step 76, the receptacle 18, with the device requiring hydration and the container 16, are placed inside the package and on top of the support base. The receptacle 18 is positioned on the support base such that the hydrate inside the container 16 would flow away from the container 16 and toward the device, if the hydrate is released from the container 16.

At step 78, an activating member 14 may be placed on top of the receptacle 18. The activating member may be pushed by an external force to crush, pierce, squeeze or otherwise cause the container to release the hydrate.

At step 80, the package is sealed. If the package and its contents have been sterilized, the package may be hermetically sealed so that the effects of sterilization are not compromised At step 82, the package and all elements contained within the package are sterilized. Any suitable technique may be used to sterilize the package and its contents. For example, the package and its contents may be exposed to ethylene oxide (EtO) or may be irradiated. If the device requiring hydration is an in vivo sensing element, such as, for example, a glucose oxidase enzyme, a protein or antibody element, the sensing element will then be suitable for in vivo implantation.

However, EtO sterilization may be detrimental to the hydrate. For example, if the hydrate is a sterilized buffer, exposure of the sterilized buffer to EtO may turn the sterilized buffer into a toxic fluid. If the sterilized buffer were to become toxic, it would be unsuitable for hydration of the device, especially if the device were an in vivo sensing element. Accordingly, when using EtO as a sterilant or other sterilizing agent for the package and its contents, the container containing the hydrate should be sufficient to protect the hydrate from contamination by the sterilant. Accordingly, the container may be made, for example, from a non-porous material. For example, if the hydrate is contained in a glass ampule, the deleterious effects that exposure of the hydrate to EtO or other sterilant may be minimized. For a light sterilant or chemical sterilant, the container may be made, for example, from foil or treated glass.

At step 84, the activating member 14 is activated to release hydrate to device. For example, activation of the activating member may be as simple as pushing on an external portion of the package with a thumb or finger such that the force of the pushing is transferred through the package to the receptacle 18, then through the receptacle 18 to the container 16 to crush the container 16 or otherwise expel hydrate from the container 16. When the hydrate is released from the container 16 in embodiments of the invention relying on gravity, the hydrate will travel toward the device requiring hydration due to the slope of the base 50 on which the receptacle 18 sits. For other embodiments of the invention, valves or other devices may be used to hydrate the device. In still other embodiments of the present invention, the system may be fabricated so that air is expelled to fully hydrate the device.

If the container is a bladder, the activating member may be a piercing element such that an external force applied to the package causes the piercing member to pierce through or puncture the receptacle and the bladder, thereby release the hydrate within the bladder to the device.

As an alternative to activation of the activating member by manual means, for example, the activating member could be subjected to a mechanical force exerting device and be activated automatically. For example, rollers, punches or the like may be used to exert a mechanical force.

The container 16 may contain elements other than a hydrate. For example, rather than a hydrate, the container 16 may contain a sterilizing agent, an activating agent such as, but not limited to, a catalyst, a cleaning agent, a coloring agent or the like. Embodiments of the present invention may be used to not only hydrate devices, but to provide any type of interaction between a device and the element contained within the container 16. For example, a coloring agent may be contained within the container 16 such that, when the activating member 14 is activated within the container 16, a liquid-liquid, liquid-powder, liquid-solid or the like chemical reaction begins, thereby providing a visual change. In other embodiments, a cleaning agent may be contained within the container 16 such that, when a force is exerted on the activating member 14, the container releases the cleaning agent to the device, thereby cleaning the device.

Figure 11:
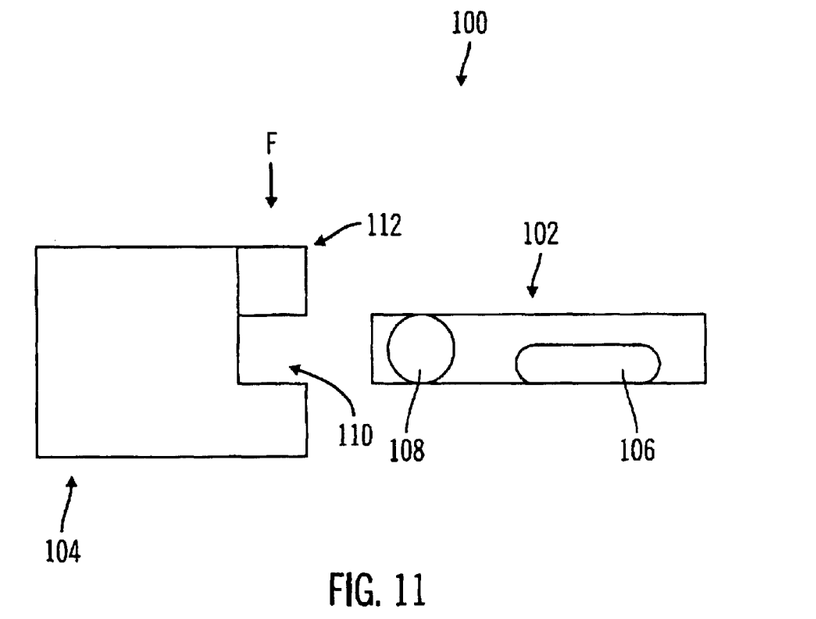
FIG. 11 shows a plan view of a generalized packaging system according to another embodiment of the present invention.

A generalized packaging system 100 according to an embodiment of the present invention is shown in FIG. 11. The packaging system 100 includes, without limitation, an enclosure 102, an activating member 112, a substance container 108 and a receptacle 104 that includes an aperture 110. The enclosure 102 may allow sterilant penetration, but not microbe penetration, and generally includes enough space within its interior to house a device requiring hydration 106 in addition to the other elements of the packaging system 100. For example, in the embodiment shown in FIG. 11, the device requiring hydration 106 may be a catheter having a sensing element which must be hydrated.

Operation of the packaging system 100 shown in FIG. 11 may be as follows. A sterilant or other hydrant may be contained in the substance container 108. When it is desired to hydrate the device requiring hydration 106, the enclosure 102, which is sealed, may be inserted into the aperture 110 located in the receptacle 104 so that the substance container 108 is disposed below the activating member 112. A force F may then be exerted upon the activating member 112 such that it crushes the substance container 108, thereby releasing the hydrant contained within the substance container 108, without compromising the integrity of the enclosure 112. The hydrant may then inundate the device requiring hydration 106, thereby hydrating the device 106, without exposing the device 106 to external contaminants.

Figure 12:
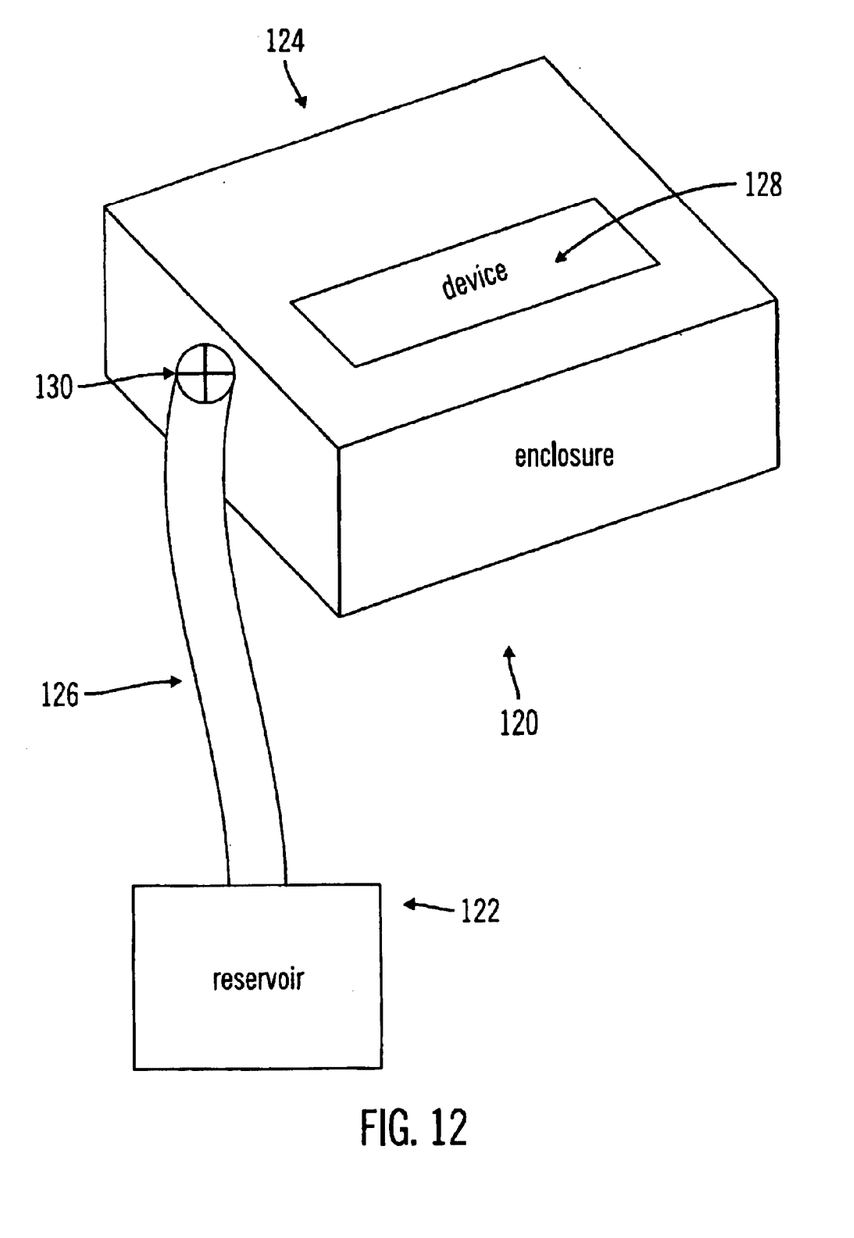
FIG. 12 shows a perspective view of a generalized packaging system according to an embodiment of the present invention.

A generalized packaging system 120 according to another embodiment of the present invention is shown in FIG. 12. The packaging system 120 includes, without limitation, an enclosure 124, a reservoir 122 containing a sterilant or other hydrate, a tube 126 and a valve 130. The enclosure 124 may allow sterilant penetration, but not microbe penetration, and generally includes enough space within its interior to house a device requiring hydration 128 in addition to the other elements of the packaging system 120. For example, in the embodiment shown in FIG. 12, the device requiring hydration 128 may be a catheter having a sensing element which must be hydrated.

In the embodiment of the invention shown in FIG. 12, the reservoir 122 containing the sterilant or other hydrate resides outside the enclosure 124. The sterilant may be released from the reservoir 122 through the tube 126 by operation of the valve 130 and into the enclosure 124, thereby hydrating the device requiring hydration 128. The tube 126 or valve 130 may then be sealed, for example, by heat sealing or other methods, so that the enclosure 124 is sealed off from external contaminants.

According to embodiments of the present invention, air may be expelled from the enclosure within which the device requiring hydration is disposed. By expelling air from the enclosure, the device requiring hydration may be effectively hydrated.

Embodiments of the packaging system described herein may be employed in a variety of applications. For example, if the device requiring hydration is an in vivo sensing element that has been sterilized and the package has been hermetically sealed, the device manufacturer could then hydrate the sensing element after sealing the package by activating the activating member through the package. Because there is no need to open the package to hydrate the sensing element, the sterilization of the sensing element need not be compromised.

If the device requiring hydration is some other element that requires hydration for activation, the user could order and store a plurality of the packaging systems and activate the activating member only when the device is needed. For devices whose efficacy slowly diminishes over time once they have been hydrated, the shelf life of such devices will have been greatly increased. The devices may remain on the shelf in an inactivated state. The devices may then be hydrated by activating the activating member through the package at such time as they are needed.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A packaging system for hydrating at least one selected portion of a device, the packaging system comprising:
   an enclosure for enclosing at least one selected portion of a device, the at least one selected portion of the device requiring hydration;
   a container containing a hydrate;
   a receptacle within the enclosure and having an interior; and
   wherein the container is operable to release the hydrate;
   wherein the container and the at least one selected portion of the device located within the interior of the receptacle are arranged relative to each other in a manner such that upon the release of the hydrate from the container, the hydrate travels by gravity toward the at least one selected portion of the device; and
   wherein the arrangement of the container and the at least one selected portion of the device exposes the at least one selected portion of the device to the hydrate while inhibiting exposure of other portions of the device to the hydrate.

2. The packaging system of claim 1, further comprising an activating member located within the interior of the enclosure for exerting a force on the container to release the hydrate to the at least one selected portion of the device.

3. A packaging system for hydrating a device, the packaging system comprising:
   an enclosure for enclosing the device requiring hydration;
   a container containing a hydrate, the container located within the packaging system adjacent to the device, wherein the container is operable to release the hydrate to the device;
   a receptacle disposed within the enclosure;
   an activating member located within the interior of the enclosure for exerting a force on the container to release the hydrate to the device; and
   a base having an inclined surface disposed within the enclosure,
   wherein the container and the device are located within an interior portion of the receptacle; and
   wherein the receptacle is disposed on the inclined surface of the base.

4. The packaging system of claim 2, wherein the activating member is located on top of the receptacle.

5. The packaging system of claim 2, wherein the force is applied to an external portion of the enclosure and is transferred to the container via the activating member.

6. The packaging system of claim 1, further comprising a covering surrounding the container.

7. The packaging system for hydrating a device, the packaging system comprising:
   an enclosure for enclosing the device requiring hydration;
   a container containing a hydrate, the container located within the packaging system adjacent to the device;
   a receptacle disposed within the enclosure; and
   a covering surrounding the container; wherein the container is operable to release the hydrate to the device; wherein the container and the device are located within an interior portion of the receptacle; and wherein the covering is a mesh.

8. The packaging system of claim 7, wherein the mesh is nylon.

9. The packaging system of claim 1, wherein the container is an ampule.

10. The packaging system of claim 1,
    wherein the at least one selected portion of the device resides in a first interior portion of the receptacle;
    wherein the container resides in a second interior portion of the receptacle; and
    wherein, upon release from the container, the hydrate flows from the second interior portion of the receptacle to the first interior portion of the receptacle through a channel.

11. The packaging system of claim 1,
    wherein the portion of the device resides in a first interior portion of the receptacle;
    wherein the container resides in a second interior portion of the receptacle; and
    wherein, upon release from the container, the hydrate flows from the second interior portion of the receptacle to the first interior portion of the receptacle through a valve.

12. The packaging system of claim 1, wherein the container is a bladder.

13. The packaging system of claim 1, wherein the container is a sponge.

14. The packaging system of claim 1, wherein the hydrate is a fluid.

15. The packaging system of claim 1, wherein the hydrate is a gel.

16. The packaging system of claim 1, wherein the hydrate is a sterilant.

17. A packaging system for bringing first and second elements located in a package into contact with each other, the packaging system comprising:
    a container containing a first element;
    a receptacle having an interior; and
    an enclosure for enclosing the receptacle, the enclosure having an interior;
    wherein the container is operable to release the first element;

wherein the container and at least one selected portion of a second element are arranged relative to each other within the interior of the receptacle in a manner such that upon the release of the first element from the container, the first element travels by gravity toward the at least one selected portion of the second element; and wherein the arrangement of the container and the at least one selected portion of the second element exposes the at least one selected portion of the second element to the first element while inhibiting exposure to the first element of other portions of the second element.

18. A packaging system for bringing elements located in a package into contact with each other, the packaging system comprising:

an enclosure for enclosing a first element;

a container containing a second element, the container located within the package adjacent to the first element;

a receptacle disposed within the enclosure; and a base having an inclined surface located within the enclosure;

wherein the container is operable to release the second element to the first element;

wherein the container and the first element are located within an interior portion of the receptacle; and wherein the receptacle is supported on the inclined surface of the base.

19. A packaging system for bringing elements located in a package into contact with each other, the packaging system comprising:

an enclosure for enclosing a first element;

a container containing a second element, the container located within the package adjacent to the first element; and a receptacle for capturing the second element upon release of the second element from the container;

wherein the container and the enclosure are arranged relative to each other such that upon release of the second element from the container, the second element travels by gravity to and contacts the first element while the first element is enclosed within the enclosure, and wherein the receptacle is arranged relative to contain the second element after the second element has come into contact with the first element.

20. The packaging system of claim 19, further comprising:

an activating member for causing the container to release the second element to the first element.

21. The packaging system of claim 1, further comprising a reservoir located in the interior of the receptacle, the reservoir having an interior, wherein the interior of the reservoir is separated from the other portions of the device.

22. The packaging system of claim 21, wherein hydrate released from the container accumulates by gravity in the interior of the reservoir.

23. The packaging system of claim 17, further comprising a reservoir located in the interior of the receptacle, the reservoir having an interior, wherein the interior of the reservoir is separated from the other portions of the second element.

24. The packaging system of claim 23, wherein the first element released from the container travels by gravity to the interior of the reservoir.

25. A packaging system for hydrating an end portion of a catheter at which a hydratable element is disposed, the end portion of the catheter extending less than the entire length of the catheter adjacent to a distal end of the catheter, the packaging system comprising:

a container containing a hydrate;

a receptacle having an interior for receiving the container and the end portion of a catheter while the rest of the catheter is disposed outside of the receptacle; and an enclosure for enclosing the receptacle, the enclosure having an interior;

wherein the container is operable to release the hydrate to the end portion of the catheter when the end portion of the catheter is received within the receptacle; and wherein, the container is arranged relative to the receptacle such that upon the release of the hydrate from the container, the hydrate travels toward the end portion of the catheter, contacts the end portion of the catheter and is inhibited from contacting other portions of the catheter when the end portion of the catheter is received within the receptacle.

* * * * *